United States Patent [19]

Chapelon et al.

[11] Patent Number: 5,720,287
[45] Date of Patent: Feb. 24, 1998

[54] THERAPY AND IMAGING PROBE AND THERAPEUTIC TREATMENT APPARATUS UTILIZING IT

[75] Inventors: Jean-Yves Chapelon, Villeurbanne; Emmanuel Blanc, Saint Genis-Laval; Francois Lacoste, Rueil, all of France

[73] Assignee: Technomed Medical Systems, Vaux En Velin, France

[21] Appl. No.: 659,581

[22] Filed: Jun. 6, 1996

Related U.S. Application Data

[63] Continuation of Ser. No. 586,662, Jan. 25, 1996.

[30] Foreign Application Priority Data

Jul. 26, 1993 [FR] France ................................ 93 09158
Feb. 4, 1994 [FR] France ................................ 94 01304

[51] Int. Cl.$^6$ ....................................................... A61B 8/12
[52] U.S. Cl. ........................... 128/660.03; 128/662.03; 128/662.06; 607/97; 601/2
[58] Field of Search .................... 128/660.01, 660.03, 128/662.03, 662.06; 601/2, 3; 600/102, 160; 607/97; 310/369

[56] References Cited

U.S. PATENT DOCUMENTS 5,469,852  11/1995  Nakamura et al.

FOREIGN PATENT DOCUMENTS 9215253  9/1972  WIPO.
9407418  4/1994  WIPO.
9502994  2/1995  WIPO.

OTHER PUBLICATIONS

International Preliminary Examination Report (Sep. 4, 1995) from PCT Application Serial No. PCT/FR94/00936.

Primary Examiner—William E. Kamm
Assistant Examiner—Shawna J. Shaw
Attorney, Agent, or Firm—Cohen, Pontani, Lieberman & Pavane

[57] ABSTRACT

The therapy and imaging probe of the invention comprises a probe body (20') of an elongate shape defining a general axis (X—X), one imaging transducer (40') for transmitting imaging waves, and one therapy transducer (30') for transmitting therapy waves. The imaging transducer is mounted on first support means providing translational movement of the imaging transducer within the probe, parallel to the general axis (X—X) of the probe, between a withdrawn position and an extended position. The therapy transducer is mounted on second support means providing rotation of the therapy transducer within the probe, about an axis of rotation (X1—X1) parallel to the general axis (X—X) of the probe but offset with respect to the imaging transducer, to allow rotation of the therapy transducer between a withdrawn position and a treatment position. In the withdrawn or non-active position of the therapy transducer, the imaging transducer may be brought by translational movement to its extended position to occupy the place occupied by the therapy transducer in its treatment position. Thus, the imaging transducer may form an image of a region for treatment by the therapy transducer. In the treatment position of the therapy transducer, the imaging transducer is at its withdrawn position. The therapy transducer, during the transmission of therapy waves, directly transmits the therapy waves in a direction substantially identical to the direction in which the imaging transducer transmits the imaging waves when imaging waves are being transmitted.

30 Claims, 8 Drawing Sheets

THERAPY AND IMAGING PROBE AND THERAPEUTIC TREATMENT APPARATUS UTILIZING IT

The present application is a Continuation of U.S. Ser. No. 08/586,662, filed Jan. 25, 1996.

BACKGROUND OF THE INVENTION

The present invention relates to an endocavital therapy (or treatment) and imaging (or visualization) probe comprising a probe body, at least one imaging transducer for transmitting imaging waves and at least one therapy transducer for transmitting therapy waves, both mounted movably within said probe, driving means for said imaging transducer and driving means for said therapy transducer.

It also relates to therapeutic treatment apparatus in which said probe is used.

Therapeutic treatment apparatuses comprising a combination of a therapy transducer and an imaging (or visualization) transducer, generally of the extracorporeal type, have been known for many years in the art. Reference may be made in this matter to U.S. Pat. No. 4,658,828 in the name of Dory.

Extracorporeal treatment devices of the prior art generally give satisfaction, but all access routes are not always possible. Firstly, it may difficult, with an extracorporeal treatment device, to carry out treatment of tissue situated deeply within the body of a human being, bearing in mind that the ultrasound therapy waves will have to pass through healthy tissue regions that need to be preserved. Because of this, it is generally desirable to employ endocavital probes for more accurate and reliable treatment of only that tissue that is to be treated.

Treatment or therapy probes already exist, as do treatment and imaging probes.

EP-A-0,317,049 discloses an ultrasound probe having a window surrounding an ultrasound transducer. The ultrasound transducer is mounted on a first circular platform designed to pivot around one of its diameters. This platform is mounted on a second circular platform designed to rotate in its plane, about its axis. In this way, the ultrasound transducer is able to scan or sweep angular sectors in all planes. The probe in EP-A-0,317,049 is designed to provide imaging of tissue surrounding the probe.

FR-A-2,673,542 discloses an endorectal therapy probe and a tumor tissue destruction apparatus, particularly for the prostate, including application thereof. The destruction apparatus in that document incorporates such an endorectal probe and an ultrasound scanning endo-urethral probe. The endorectal therapy probe includes a piezoelectric transducer having a forward ultrasound acoustic wave transmission face, mounted in a support body linked to rigid guiding means enabling the probe to be introduced endorectally. The complete assembly thus constituted is surrounded by a deformable silicone or latex membrane designed to be filled with a FR-A-2,673,542 discloses a solution to the problem of destroying tumor tissue, allowing real-time monitoring. The solution disclosed consists in using an ultrasound imaging endo-urethral probe.

The solution disclosed there suffers from certain disadvantages. Firstly, it involves simultaneous use of an endo-urethral probe and an endorectal probe which increases the traumatic effect. It is also necessary to move the two probes for the requirements of echographic examination and of treatment. This adds to the traumatic effect. The accuracy of the apparatus is limited by the mechanical accuracy of the common support means for the endorectal probe and the endourethral probe. To achieve good accuracy, it is necessary to employ complex mechanical systems. Should the latex or silicone envelope of the endorectal probe rupture, the continuation of movement can be the source of significant trauma. Finally, the combination of endorectal and endo-urethral probes does not allow real time visual monitoring, the echography transducer being saturated for reception when the treatment wave is transmitted.

Figure 5:
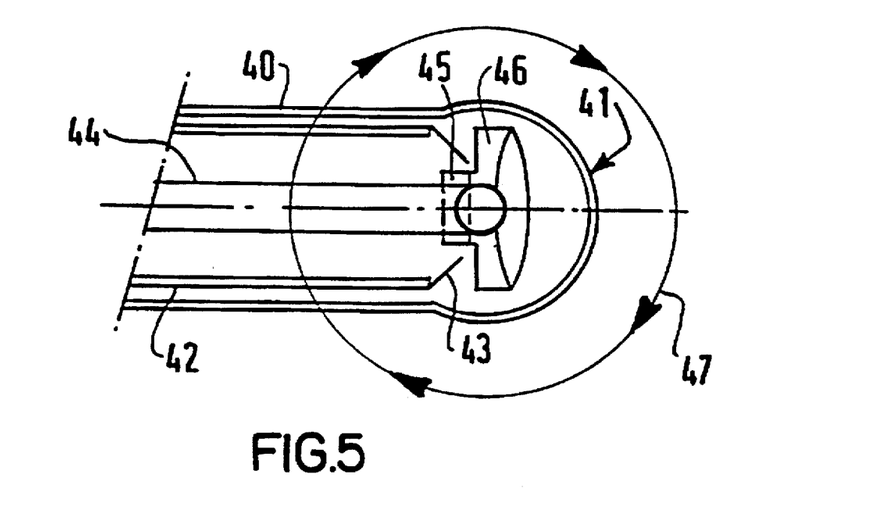
FIG. 5 is a similar view to that in FIG. 2 of yet a further embodiment of the invention.

WO-A-89/07909 discloses, in particular with reference to FIG. 5, an endorectal locating and therapy probe. This probe comprises a focusing transducer designed to transmit ultrasound for imaging or viewing purposes. The transducer is mounted on a shaft that is able to move with respect to the flexible outer casing of the probe. The probe further includes a focusing transducer for therapy, which is pivotally mounted about one of its diameters on arms that are movables with respect to the flexible outer casing of the probe. The therapy transducer transmits towards a redirecting mirror which reflects the ultrasound into the region to be treated.

This device suffers from disadvantages. It is bulky due to the large number of parts included. It further includes numerous mechanical devices for which a high degree of accuracy is difficult to obtain. The same danger exists here as applies in the case of the apparatus of EP-A-0,317,049 should the outer flexible envelope tear.

The combination, in the case of the endocavital probe of the latter patent, of a therapy transducer and an imaging transducer involves complex solutions, notably considering that the therapy transducer delivers ultrasound waves which need to be reflected by a redirecting mirror onto the tissue to be treated. Due to the presence of this mirror it is impossible to find an optimum aperture ratio to provide optimum concentration of the ultrasound waves at the focus thereof, remembering that the aperture ratio of the therapy transducer is given by the ratio of diameter to focal length. Because of this, in the framework of this prior art device, it is physically impossible to obtain a therapy transducer aperture ratio close to 1, or even greater than 1. This involves a supplementary limitation to therapeutic performance.

SUMMARY OF THE INVENTION

The present invention overcomes these disadvantages. It provides a simple, reliable, and less traumatic solution to imaging and tissue treatment; it is particularly suitable for prostate treatment. The present invention, notably when compared to the prior art comprised by WO-A-89/07909 enables a probe that is less bulky to be obtained without any reduction in the effectiveness and accuracy of treatment and imaging.

The present invention also sets out to resolve the new technical problem consisting in providing a solution able to provide an endocavital probe that combines a therapy transducer and an imaging transducer, in which the therapy transducer has an aperture ratio defined as the diameter/focal length ratio which is as high as possible, if possible close to 1 and even greater than 1 thus obtaining a maximum concentration of ultrasound waves at the region of the focus, with greatly improved effectiveness of therapy.

In one embodiment, a further aim of the invention is to resolve the new technical problem consisting of supplying a solution able to provide an endocavital probe that combines a therapy transducer and an imaging transducer, that enables the perimeter of the endocavital probe in a plane perpendicular to the axis of introduction to be reduced while still maintaining optimum aperture of the therapy transducer, while simultaneously ensuring the imaging transducer can be positioned at the exact place of, and as a replacement for, the therapy transducer in order to obtain an image of the tissue to be treated at one single position of the endocavital probe body, whether this be for imaging or for therapy purposes.

In one embodiment, a further aim of the invention is to resolve the new technical problem consisting in the need to provide an endocavital probe in which a therapy transducer and imaging transducer are combined, having an optimum aperture for effective treatment, in which movement of the therapy transducer is reduced to a limited amount, said transducer notably only performing rotary movement, in particular about an axis of rotation that is parallel to the axis of introduction of the endocavital probe for higher therapy accuracy. Advantageously, this technical problem should be resolved by a solution that avoids translational movement of the body of the endocavital probe between the imaging phase and the therapy phase, to avoid all risk of moving the therapy tissue region, such as an organ.

A further aim of the invention is to resolve the new technical problems stated above by a solution that enables an independent imaging probe to be used, allowing any type of commercially-available imaging probe to be employed, thus reducing in The present invention makes it possible, for the first time, to simultaneously resolve the technical problems stated above in a simple, reliable, reproducible and relatively inexpensive fashion, that can be employed on an industrial and medical scale.

The invention provides a therapy and imaging endocavital or intraluminal probe comprising a probe body, at least one imaging transducer for transmitting imaging waves and at least one therapy transducer for transmitting therapy waves, both mounted movably within said probe, driving means for said imaging transducer and driving means for said therapy transducer, in which said therapy transducer and said imaging transducer are movably mounted within said probe whereby said therapy transducer, during the transmission of therapy waves, directly transmits said therapy waves in a direction substantially identical to the direction in which said imaging transducer transmits said imaging waves when imaging waves are being transmitted.

The invention provides a probe that has a simple mechanical structure, is less bulky, and may incorporate a wide-aperture therapy transducer.

According to one embodiment the imaging and therapy transducers are movable about a common axis of rotation, the driving means being common to said imaging transducer and said therapy transducer.

In this way, it is easy to change from treatment mode to imaging mode and vice-versa. This does not involve any movement of the probe, and guarantees excellent treatment accuracy. Moreover, it limits the number of moving mechanical elements present in the probe.

In one embodiment of the probe, said common axis of rotation is parallel to the longitudinal axis of the probe.

This is particularly suited to the case of endorectal probes intended for imaging and/or treatment of the prostate.

In another embodiment of the probe, said common rotation axis is orthogonal to the longitudinal axis of the probe.

This allows treatment and/or visualization in a region situated on the longitudinal axis of the probe. The treatment transducer and the imaging transducer may take the form of a one-piece assembly.

In this case, accuracy upon changeover from treatment to imaging depends only on the quality of assembly of said one-piece structure.

In a simple embodiment, said treatment transducer and said imaging transducer each are disc-shaped and are arranged concentrically and back-to-back.

The treatment transducer may have a concave shape ensuring focusing.

The probe may comprise a second therapy transducer having a recess at its center in which the imaging transducer and the therapy transducer are arranged.

This enables the bulkiness of the probe to be reduced without sacrificing treatment efficiency.

According to one embodiment, the endocavital probe is of an elongate shape defining a general axis for introduction into a body cavity; furthermore:

the imaging transducer is mounted on first support means providing translational movement of the imaging transducer substantially parallel to the general axis of the endocavital probe, between a withdrawn position and an extended position;

the therapy transducer is mounted on second support means providing rotation of the therapy transducer about an axis of rotation substantially parallel to the general axis of the probe but offset with respect to the imaging transducer, preferably outside the largest dimension of the imaging transducer to allow rotation of the therapy transducer between a withdrawn or non-active position for which the imaging transducer may be brought by translational movement to the extended position to occupy the place previously occupied by the therapy transducer, in order to enable the imaging transducer to form an image of a region for treatment by the therapy transducer, and a treatment position for which the imaging transducer is at a withdrawn position, thus making it possible to view and treat the target region from the same position of the endocavital probe.

In one advantageous embodiment, the therapy transducer and the imaging transducer are arranged inside a flexible membrane filled with an acoustic-coupling liquid such as water or an oil.

In another advantageous embodiment, the therapy transducer is mounted in a support member integral with second support means having a cross-section in a plane perpendicular to the general axis of the probe defining a perimeter which is as close as possible to the perimeter of a cross-section taken in the same plane of the therapy transducer.

In a further advantageous embodiment, the external shape of the therapy transducer is that of a disc, the profile of which is for the major part substantially circular, but having a reduced diameter in a direction perpendicular to the general axis of the probe.

In yet a further advantageous embodiment, the imaging transducer is arranged to provide images in several planes, in particular in two perpendicular planes, comprising a first plane, or radial plane, perpendicular to the general axis of the probe, and a second plane, or sagittal plane, containing the general axis thereby making it, in particular, possible to also provide imaging of the treatment region during the course of treatment.

According to another advantageous embodiment, the therapy transducer is arranged to provide focusing in a direction substantially perpendicular to the general axis of introduction into a body cavity.

In a particularly advantageous embodiment, the said support member for the therapy transducer has a substantially circular or polygonal outside shape, close to the outer shape of a substantially circular or polygonal-shaped therapy transducer, the therapy transducer support member being integral with the second support means close to an edge thereby facilitating movement of the therapy transducer between the withdrawn position and a treatment position.

In a currently preferred embodiment, the outer shape of the therapy transducer defines an axis of symmetry which is substantially parallel to the abovesaid axis of introduction.

In one advantageous embodiment, when the therapy transducer is externally disc-shaped, with an outer profile that is for the most part circular, and in particular in the optional embodiment in which it exhibits a reduced diameter in a direction perpendicular to the axis of introduction, an axis of symmetry of said transducer is substantially parallel to the said axis of introduction.

According to one advantageous feature, the imaging transducer constitutes part of an independent imaging traducer which preferably consists of any type of commercially-available probe, the latter being advantageously able to provide images in several planes, particularly two planes as mentioned above.

According to one advantageous feature of the invention, the therapy transducer has an aperture ratio, in other words a ratio between diameter and focal length comprised between 0.8 and 1.5, and more preferably around 1, thus providing a determining advantage at the time of therapy of increased effectiveness in the focal region and an absence of secondary lesions in the area situated between the therapy transducer and the focal region.

According to a further preferred feature, means providing manual rotation or motor-driven rotation of the therapy transducer about an axis thereof, and means for providing manual or motor-driven translational movement of the imaging transducer are provided, rotation or translational movement being optionally provided via the abovesaid first and second support means.

The treatment transducer may also comprise a mechanically-deformable lens which allows its focal length to be varied.

This has the effect of increasing the treatment range.

In one embodiment, the treatment and imaging probe comprises a rigid wall at least partially surrounding said transducers.

This avoids all danger to the patient resulting from movement of the transducers.

In this case, said rigid wall may include a window.

Said window allows ultrasound to pass through to the patient.

In one embodiment of the invention, the treatment and imaging probe comprises a locally deformable flexible casing.

Said casing ensures contact with the treatment and/or visualization area, and thus allows ultrasound to pass through.

The invention also provides a treatment apparatus comprising an endocavital probe as defined above.

In one particular embodiment the said treatment apparatus constitutes treatment apparatus for a target region inside the body of a mammal, in particular a human being, comprising means for introducing a said probe into a body cavity. This cavity can be natural or be provisionally created by surgery, notably by incision.

In one particular embodiment, the target zone is a tissue region for treatment, in particular malignant or and non-malignant tissue, usually in the form of non-malignant or malignant tumors.

According to another embodiment of the invention, the said treatment apparatus is an apparatus for treating prostate tissue by urethral or rectal route. For treatment of prostate cancer, the rectal route is currently preferred.

The invention further relates to a method for treating a target region inside the body of a mammal, in particular a human being, comprising:

providing an endocavital probe of elongated shape defining a general introduction axis into a body cavity;

providing an imaging transducer mounted on first support means providing translational movement parallel to said general axis of said endocavital probe of the imaging transducer between a withdrawn and an extended position;

providing a therapy transducer mounted on second support means providing rotation of said therapy transducer about an axis of rotation parallel to said general axis of the endocavital probe but offset with respect to said imaging transducer, preferably externally of the widest dimension of the imaging transducer, to allow the therapy transducer to move between a retracted or non-active position in which said imaging transducer can be moved in translation into said extended position in order to occupy the place previously occupied by said therapy transducer, and a treatment position for which said imaging transducer is in a withdrawn position, introducing said endocavital probe into said body cavity until said therapy transducer is substantially facing said target region, if appropriate, rotating said therapy transducer in order to position it in said retracted non-active position;

moving said imaging transducer with a translational movement into said extended position to occupy the place of said therapy transducer, forming an image with said imaging transducer of said target region to be treated by said therapy transducer allowing said target region to be viewed, withdrawing said imaging transducer into said withdrawn position, rotating said therapy transducer to bring it to said treatment position, delivering ultrasonic treatment waves during a predetermined interval necessary for performing said treatment.

BRIEF DESCRIPTION OF THE DRAWINGS

The features and advantages of the invention will become clear from the description that follows of one embodiment of the probe according to the invention, provided by way example with reference to the attached figures. In these.

DETAILED DESCRIPTION OF PREFERRED EMBODIMENTS

The invention provides an endocavital therapy and imaging probe comprising a probe body, at least one imaging transducer for transmitting imaging waves and at least one therapy transducer for transmitting therapy waves, both mounted movably within said probe, driving means for said imaging transducer and driving means for said therapy transducer. In the probe, said therapy transducer and said imaging transducer are movably mounted within said probe whereby said therapy transducer, during the transmission of therapy waves, directly transmits said therapy waves in a direction substantially identical to the direction in which said imaging transducer transmits said imaging waves when imaging waves are being transmitted.

Thanks to the fact that the therapy transducer directly transmits therapy waves in a firing direction that is identical or substantially identical to the direction of imaging shots, no redirecting mirror is necessary. The mechanical structure of the probe is simplified. Moreover, as the probe includes fewer parts moving relative to each other, treatment accuracy and the degree of correlation between treatment and visualization are improved. The invention notably makes it possible to increase the effectiveness of treatment and to limit the bulk of the probe.

In a first family of embodiments of the invention described with reference to FIGS. 1 to 7, the transducer(s) is/are mounted on a common rotational axis. The mechanical driving means for, firstly, the therapy transducer(s) and, secondly, the imaging transducer(s) are then at least partially common. In this way, it is possible to make all the transducers turn about a common axis of rotation whereby the direction of transmission of the therapy waves and imaging waves coincide; this common direction is substantially perpendicular to the common axis of rotation.

Figure 1:
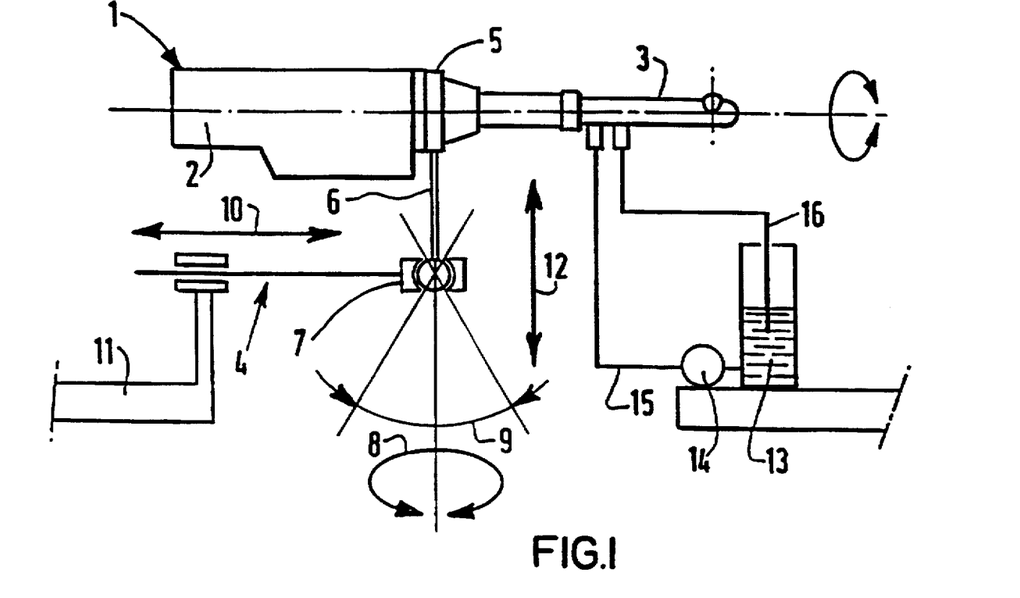
FIG. 1 is a diagrammatical overall view of a first embodiment of the probe according to the invention and of its support mechanism.

In a second family of embodiments of the invention, described with reference to FIGS. 8 to 12, the means for driving the therapy transducer(s) and imaging FIG. 1 is a diagrammatical view of a complete probe according to the invention and its support mechanism. Probe 1 has a body 2 and a head 3 designed to be introduced into the patient. The body of the probe is linked to a support mechanism 4 which allows probe 1 to be moved and/or set at a given position. The support mechanism can have any desired shape. In the embodiment of FIG. 1, the support mechanism comprises a collar 5 in which probe body 2 is mounted rotatively, and which is linked to one end of a rigid rod 6. The other end of rod 6 can move inside a swivel joint 7 which allows the probe to be moved in rotation about rod 6, or pivotally about said swivel joint, as indicated by the arrows 8 and 9 in FIG. 1. Swivel joint 7 is freely mounted in translation in accordance with arrow 10 of FIG. 1, on a support 11. Support 11 is able to move vertically in the plane of the figure, as indicated by arrow 12.

On FIG. 1, a liquid reservoir 13 associated with a pump 14 is shown. The liquid pumped by pump 14 is fed by a conduit 15 to probe 1. The liquid circuit within probe 1 will be explained in more detail with reference to FIG. 2. The liquid originating from probe 1 returns to reservoir 13 via a conduit 16.

Figure 2:
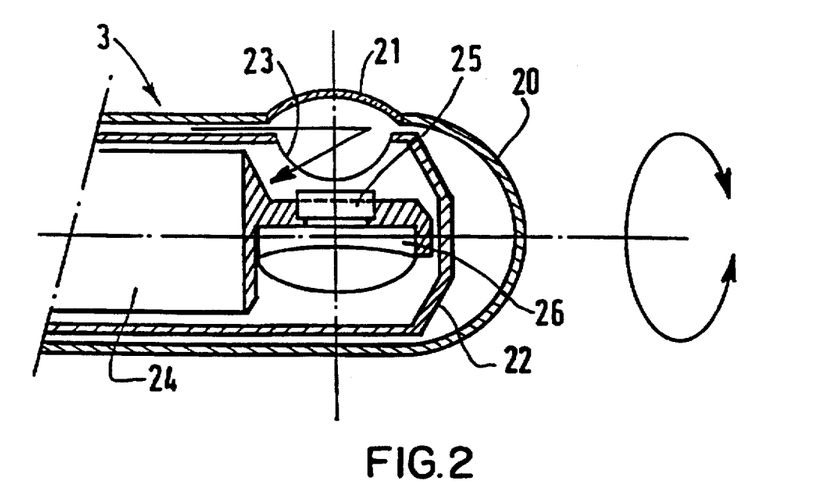
FIG. 2 is a view on a larger scale of the head of the probe in FIG. 1.

FIG. 2 is a view on a larger scale of the head of the probe in FIG. 1. This probe has a flexible casing or envelope 20 that includes a deformable region 21. This flexible casing is designed to be removable and, for example, changed for each patient. The probe has a rigid wall 22 including a window 23. Wall 22 has an elongated shape and is covered by the flexible casing 20. Deformable region 21 of the flexible casing is arranged opposite window 23 of the rigid wall. In the embodiment described with reference to FIGS. 1 and 2, window 23 is provided on the side of the probe. Other embodiments are possible as will be seen clearly from the remaining figures. Window 23 could completely surround the probe or partially extend over the circumference thereof.

Inside rigid wall 22, the probe comprises a shaft 24 rotatively mounted with respect to rigid wall 23. Shaft 24 supports an imaging transducer 25 and a treatment transducer 26 at its end, facing window 23 and deformable region 21. The probe has electrical conductors which are not shown and are linked to transducers 25 and 26 for exciting them with electrical signals. In the embodiment of FIG. 2, transducers 25 and 26 are mounted on the shaft 24 substantially symmetrically with respect to the probe axis. In other words, when imaging transducer 25 is placed opposite window 23, treatment transducer 26 points to the side opposite window 23.

In the present description, the transducers deliver ultrasound in order to view or treat the patient. Imaging and/or treatment techniques using ultrasound are described in the prior art and are known to those skilled in that art.

The imaging transducer is for example composed of a piezo-composite transducer of 10 mm diameter, of focal length 45 mm with a resonant frequency of 7.5 MHz. The treatment transducer has a concave shape and focuses the ultrasound. It can for example consist of a 25 mm diameter transducer with a focal length of 50 mm and resonant frequency of 3.5 MHz.

The circulation of liquid inside probe 1, mentioned above, is carried out in the following manner. The liquid originating from the pump is pumped between rigid wall 22 and flexible casing 20. It passes through window 23, penetrates inside rigid wall 22 and flows towards the reservoir, passing between shaft 24 and wall 23. The transducers are cooled by the fluid flow in the probe. This flow also ensures the deformable region 21 is inflated and thus comes into contact with the patient's tissue. Such contact ensures the ultrasound delivered by the transducers passes to the region do be treated.

The probe in FIGS. 1 and 2 is particularly suited to prostate treatment by rectal route. The use thereof will be described below using as an example treatment of the prostate. The probe operates in the following manner: the probe is firstly introduced in the patient's rectum so that window 23 is in the neighborhood of the prostate. The flexible casing is then inflated by supplying liquid from the pump. The deformable region of membrane 21 comes into contact with the patient's tissue thus allowing the ultrasound to pass to the region to be treated and/or viewed. Next, the region to be treated is visualized. The imaging transducer is used for this. The imaging transducer can be used in mode A echography by placing the transducer opposite the window 23 by rotating shaft 24 and then keeping it stationary. Echographic scanning or sweep is then provided by rotating shaft 24. This enables mode B echographic images to be obtained. The width of sweep depends on the size of window 23 which can be suitably adapted. In the embodiment of FIG. 1, the images are taken in a plane orthogonal to the probe axis.

Once the treatment regions have been visualized and located, all that is required in order to change over to treatment mode is to rotate shaft 24 in order to position the treatment transducer 26 opposite window 23 and opposite the region to be treated. This does not involve any movement of the probe: actually, it is only shaft 24 that rotates inside rigid wall 23. The invention thus makes it possible to overcome the lack of accuracy of prior art devices: accuracy does not depend on a mechanical positioning of two devices, nor does it depend on a mechanical displacement of the probe. According to the invention, accuracy when changing over from imaging mode to treatment mode is only limited by the degree of accuracy of the relative positioning of transducers 25 and 26 and by the degree of accuracy of Changeover from treatment mode to imaging mode is also simple. All that is required is again to situate the imaging element opposite window 23. This ensures a high degree of flexibility when changing from treatment to imaging mode and vice-versa.

The invention also provides a device with enhanced safety. Even if flexible casing 20 were to tear or break, parts that were possibly moving, in other words shaft 24 carrying the transducers, remain inside the rigid wall; there is thus no danger of their wounding the patient.

According to the invention, one can quickly change over at will from treatment to imaging mode. Treatment can consist of delivery of treatment ultrasound alternating with delivery of imaging ultrasound, which allows progression of treatment to be followed in real time. One can also chose to examine the treated region from time to time, as a checking measure.

In one embodiment of the invention, therapy transducer 26 is provided, on its transmission face, with a pocket of liquid having a different refractive index, and which is designed to be inflated to a greater or lesser extent thus varying the focal length of transducer 26. This pocket acts in combination with deformation of deformable region 26 of flexible casing 20, for varying the focal length of the therapy transducer. It is thus possible, thanks to the invention, to treat tumors at varying depths without mechanically moving the probe. This will become more clear from the description accompanying FIG. 7.

Figure 3:
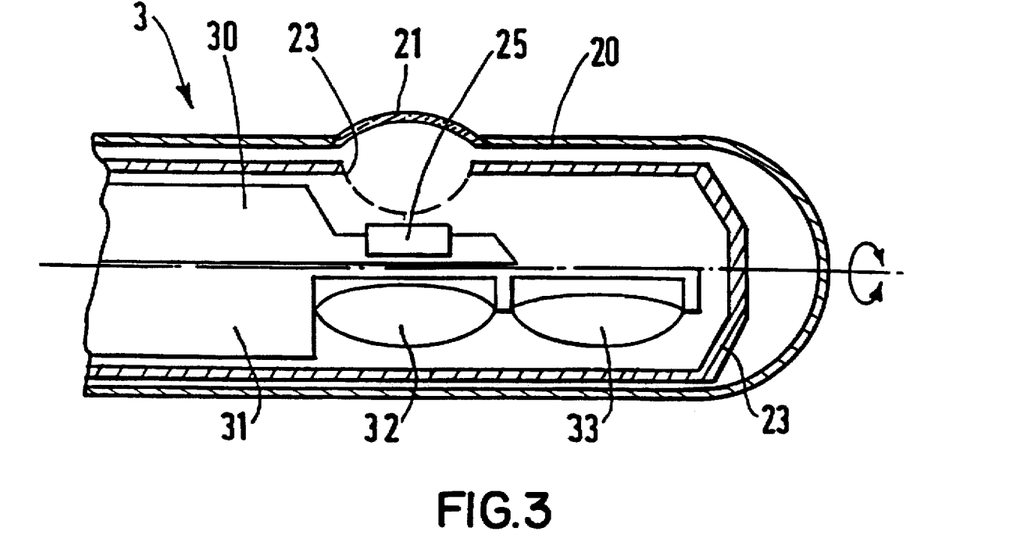
FIG. 3 is a view similar to that in FIG. 2 of another embodiment of the probe according to the invention.
Figure 4:
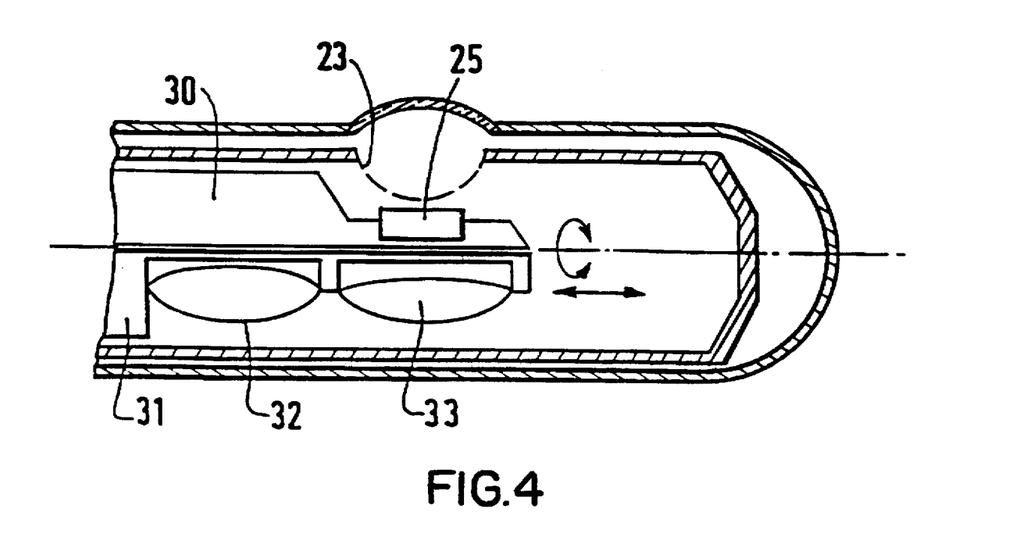
FIG. 4 shows the probe of FIG. 3 set for a different depth of treatment.

FIG. 3 is a similar view to that in FIG. 2 of another embodiment of the invention. Identical references identify the same elements, and their description will not be repeated. The probe in FIG. 3 is substantially identical to the one in FIG. 2. However, the probe in FIG. 3 has, instead of single shaft 24 supporting the transducers, two half-shafts 30 and 31; half-shaft 30 supports imaging transducer 25. Half-shaft 31 supports two therapy transducers 32 and 33. The two transducers 32 and 33 have different focal lengths. In the embodiment of FIGS. 3 and 4, it is possible to modify further the depth of fire. Half-shaft 31 is in fact designed to be displaceable longitudinally along its longitudinal axis with respect to half-shaft 30. This ensures that transducer 32 or transducer 33 can be brought behind the imaging transducer, facing window 23.

In FIG. 3, therapy transducer 32 is situated at the level of imaging transducer 25. In this way, by combined rotation of half-shafts 30 and 31, imaging and treatment at a depth corresponding to the focal length of transducer 32, optionally corrected by an inflatable lens, is ensured.

FIG. 4 is a view of the probe in FIG. 3, set for a different therapy depth. Half-therapy transducer 33 to window 23. As explained with reference to FIG. 3, combined rotation of the two half-shafts 30 and 31 makes it possible then to view and provide treatment at a depth corresponding to the focal length of transducer 32.

The probe for imaging mode described with reference to FIGS. 3 and 4 operates like the probe described with reference to FIGS. 1 and 2. It enjoys the same advantages and further makes it possible to carry out ultrasound treatment over a wide range of depths.

FIG. 5 is a similar view to that in FIG. 2 of yet a further embodiment of the invention. The probes described with reference to FIGS. 1 to 4 were particularly suited to imaging and treating tissue situated in a lateral position with respect to the probe; in particular, the use thereof as an endorectal probe allowed prostate treatment. The probe in FIG. 5, is, on the contrary, designed to view and treat tissue situated along the longitudinal axis of the probe. It is thus particularly suited to treating liver cancers or fibromas.

The probe in FIG. 5 has a similar structure to that shown in FIG. 1. Only the head of the probe is different. Because of this, only the head is shown in FIG. 5 in a cross-sectional view similar to FIG. 2. The probe has a flexible casing 40 provided at its end with a deformable region 41; the probe also has a rigid wall 42 provided at its end with a window 43. This window 43 opens on the longitudinal axis of the probe at the end thereof. Inside the rigid wall, the probe comprises two arms 44.

The probe comprises an imaging transducer 45 and a therapy transducer 46, mounted concentrically and back-to-back. The complete assembly thus obtained is mounted on the two arms 44 of the probe so as to be able to rotate about a diameter.

As shown symbolically in FIG. 5 by the arrows 47, the diameter about which the two-transducer assembly rotates is orthogonal to the axis of the probe. The probe includes electric power means for the transducers, and means for controlling rotation which are not shown in FIG. 5. Like in the case of the probe described with reference to FIGS. 1 and 2, the probe in FIG. 5 may include a fluid supply circuit for ensuring inflation, by the liquid, of the deformable region 41, and cooling of the transducers 45, 46.

The probe in FIG. 5 may provide visualization or treatment in any plane whatsoever. By rotating the complete probe assembly, the scanning or sweep plane of the probe is varied. Rotating the transducers provides scanning or treatment over the plane concerned. The probe of FIG. 5 has the same advantages as the probes described above.

The size or shape of the window 45 of the probe shown in FIG. 5 could vary from what is shown.

FIG. 6 shows various embodiments of transducers intended for probes according to the invention. FIG. 6a is a sectional view of a set of transducers for a probe according to the invention. This assembly consists of two therapy transducers 50, 51 having different focal lengths, and one imaging transducer 52. The three transducers 50, 51, 52 are mounted so that their respective diameters constitute a triangle. The set of transducers of FIG. 6a is designed to be mounted on a probe such as the one shown in FIG. 2. In this case, the assembly is mounted on shaft 24 so that the axis of shaft 24 is perpendicular to the triangle formed by the transducer diameters. Rotating shaft 24 ensures that one of the two therapy transducers, or the imaging transducer is brought in front of window 23. The set of transducers of FIG. 6a is also designed to be mounted in a probe such as the one shown in FIG. 5. In this case, the assembly is mounted between the arms 44 so that the axis of rotation is perpendicular to the triangle formed by the transducer diameters. One can then bring one of the therapy transducers, or the imaging transducer, in front of window 43.

Figure 6A:
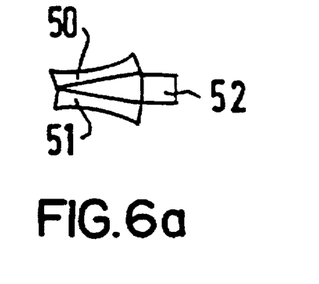
FIGS. 6a to 6d shows various embodiments of transducers.
Figure 6B:
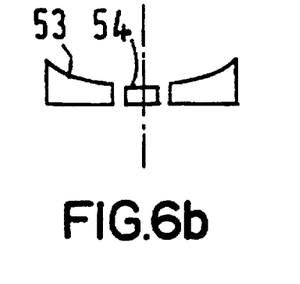

FIG. 6b is a sectional view of another embodiment of a set of transducers intended for the probe according to the invention. This set of transducers comprises a therapy transducer in the form of a disc 54, having a hollow at its center in which imaging transducer 54 is arranged. The device of FIG. 6b can be mounted in the probe of FIG. 2 in place of the transducer 26 and transducer 25. This thus provides a possibility of therapy and imaging with the advantages mentioned above. Similarly, the device in FIG. 6b can be mounted in a probe such as the one of FIG. 5.

Figure 6C:
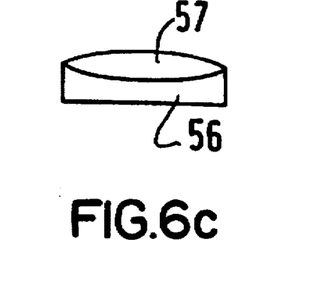

FIG. 6c is a sectional view of a therapy and imaging transducer 56; transducer 56 is simultaneously employed as a therapy transducer and imaging transducer. It further includes a lens 57 enabling its focal length to the varied. The transducer of FIG. 6c is designed to be mounted in a probe according to the invention, such as the one in FIG. 2 or the one in FIG. 7.

Figure 6D:
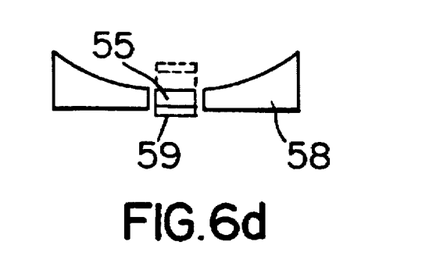

FIG. 6d is a sectional view of another set of transducers according to the present invention. The device in FIG. 6d comprises a second therapy transducer 58 having a recess at its center, like the therapy transducer in FIG. 6b. A set of transducers, consisting of a therapy transducer 55 and an imaging transducer 59 is arranged inside this recess. The set of transducers 55, 59 is rotatively mounted with respect to the second therapy transducer 58: thus, it is possible to present either transducer 55 or imaging transducer 59 to the center of the second therapy transducer 58 at the therapy ultrasound transmission side thereof. When therapy transducer 55 is directed towards the transmission side of second therapy transducer 58, as indicated by solid lines on FIG. 6d, therapy transducers 55 and 56 provide, directed towards the transmission side of second therapy transducer 58 as shown by dashed lines in FIG. 6d, it is possible to view the treated region.

In one advantageous embodiment, the device of FIG. 6d comprises means for mechanically driving the set of transducers 55, 59, and to drive them so as to cause scanning or sweep in several directions. For example, the drive means may drive the transducers 55, 59 in rotation about a common axis but also vary the angular position of said axis with respect to the probe axis. Thus, when imaging transducer 59 is directed towards the transmission side of second therapy transducer 58, imaging can be done either in a plane containing the probe axis, or in a plane that is perpendicular to said probe axis.

The embodiment of FIG. 6d makes it possible, compared to that in FIG. 6b, to increase the transmission surface of therapy ultrasound. It also makes it possible, when compared to the embodiment of FIG. 2, to decrease the bulkiness of the probe, as second therapy transducer 58 does not need to necessarily be able to perform half a rotation to provide imaging.

The second therapy transducer 58 of FIG. 6d can have any desired shape, and notably the spoon shape, which is a shape of the therapy transducer described with reference to FIGS. 8 to 14. Advantageously, transducer assembly 55, 58 has a circular shape and is arranged on the axis of the second therapy transducer 58. Common drive means drive the transducer assembly 55, 59 in rotation. It is possible to additionally provide drive means enabling simultaneous scanning or sweep of transducer 55, 58 and 59 to be performed, for example during therapy.

Figure 7:
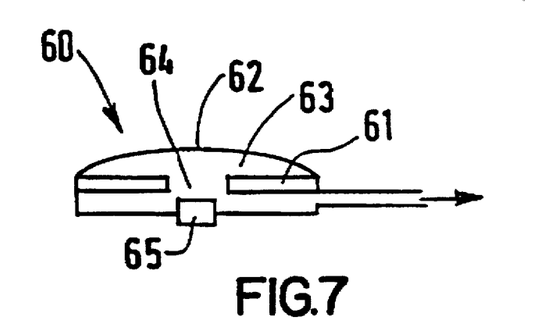
FIG. 7 is a more detailed view in cross-section of a treatment transducer with means for focusing it.

FIG. 7 is a more detailed view of a therapy transducer provided with a lens for focal length variation, according to the invention. Transducer 60 comprises a transmitting surface 61 consisting, for example, of a piezo-electric insert or element. A resilient membrane 62 that is transparent to ultrasound is stretched in front of transmitting surface 61. A liquid 63 is located between transmitting surface 61 and yielding membrane 62.

The liquid 63 exhibits a different propagation speed from that of the external medium in which the ultrasound will be propagated. In the case of a probe such as the one described with reference to FIGS. 1 to 5, the external medium consists of water, the liquid 63 having a propagation index or speed that is different from that of water. Pressurization means such as a pump, which are not illustrated, may cause the amount of liquid 63 to vary so as to modify the shape of membrane 62. This leads to a modification in the focal length of transducer 60. Under the action of the pressure of liquid 63, membrane 62 takes the form of an almost spherical cap or cup.

The insert or element 61 has a recess 64 at its center, and the small size it possible to know the position of membrane 62 along the straight line from recess 64 by calculating the time needed for an ultrasound pulse to travel through the liquid 63. Using this position, it is possible, knowing the diameter of the transmitting surface 61 to determine the radius of the spherical cap or cup formed by membrane 62, and to calculate the focal length of transducer 60. One could also determine the focal length from measurement of the pressure of liquid 63 used to inflate the membrane, after carrying out previous calibration. Obviously, transducer 60 includes means for exiting the transmitting surface 61, and piezoelectric device 65, which are not shown.

The transmitting surface 61 can have any desired shape. It can for example be concave which limits, for a given focal length, deformation of membrane 62.

The transducer 60 is designed to be employed in a probe according to the invention such as those shown in FIGS. 1 to 5.

The transducer in FIG. 7 enables the focal length of a transducer to be varied, for performing treatment at varying depth without having to move the transducer or modify the size of the ultrasound radiation entry surface in the region to be treated. This has the advantage of avoiding mechanical systems and limits the danger of burning.

By way of example, one can employ an insert or element 61 of a diameter of the order of 35 mm, having a 4 mm diameter recess at its center. The presence of the focus adjusting means makes it possible to treat depths that vary from 5 to 40 mm, equivalent to a focal length of 15 to 50 mm.

We will now describe various therapy methods which are possible using the probes according to the invention. In a first therapy mode, a shot is performed using the therapy transducer which is stationary. Following this, the imaging transducer is rotated to perform a scan and provide visualization of the treated region. Next, rotation of the transducers is stopped in order to carry out a fresh therapy shot, and so on.

In a second therapy mode, sweeping or scanning is carried out at regular intervals, in order to obtain images of the region to be treated. Between such scan or sweep operations, a plurality of therapy shots are performed. During each therapy shot, the therapy transducer is stationary. Between each therapy shot, one can optionally move the therapy transducer or vary the focal length thereof, in order to destroy an extended region.

In a third therapy mode, the transducers are driven with a continuous rotary movement, therapy or imaging shots being performed during rotation.

In a fourth therapy mode, the transducers are driven with a continuous rotary Obviously, in these two latter therapy modes, it is possible to decide whether to shoot or not during alternating or continuous rotation of the transducers.

In all the embodiments of the invention, the therapy transducer may be plane, or may be pre-focused as a result of its shape. It can be provided with a mechanical focusing device such as the one described with reference to FIG. 7. It can also be provided, if appropriate, with an electronic focusing device.

It is possible to mange the therapy and imaging transducers in configurations other than those indicated above. For example, in an embodiment similar to that in FIG. 2, a therapy transducer and an imaging transducer could be disposed at the same side of the shaft, while being slightly inclined with respect thereto. Similarly, the invention is not limited to the window shapes and sizes indicated above. The rigid wall could be transparent to ultrasound in which case the window would not be necessary.

With reference to FIGS. 8 to 12, treatment apparatus according to the invention in a presently-preferred embodiment is shown, indicated generally by reference numeral 10'. This treatment apparatus generally comprises a device forming an endocavital probe 20' comprising at least one therapy transducer 30' and one imaging transducer 40' mounted on support means such as those indicated by 50' and 60'. This treatment apparatus generally comprises a control unit 70' generally comprising a computer or microcomputer 72' fitted with all conventional peripherals such as a monitor 74', a data entry keyboard 76', and RAM and/or ROM memory means 78'. Control unit 70' is responsible for controlling translational and/or rotational motion command means 80' of the various means and/or devices of the treatment apparatus, and notably the means 82' controlling therapy ultrasound wave transmission at therapy transducer 30', as will be readily understood by those skilled in the art. Furthermore, arrangements can be made for imaging data supplied by imaging transducer 40' to be transmitted to image display means 84' such as a video monitor for subsequent transfer to control unit 70'.

Figure 8:
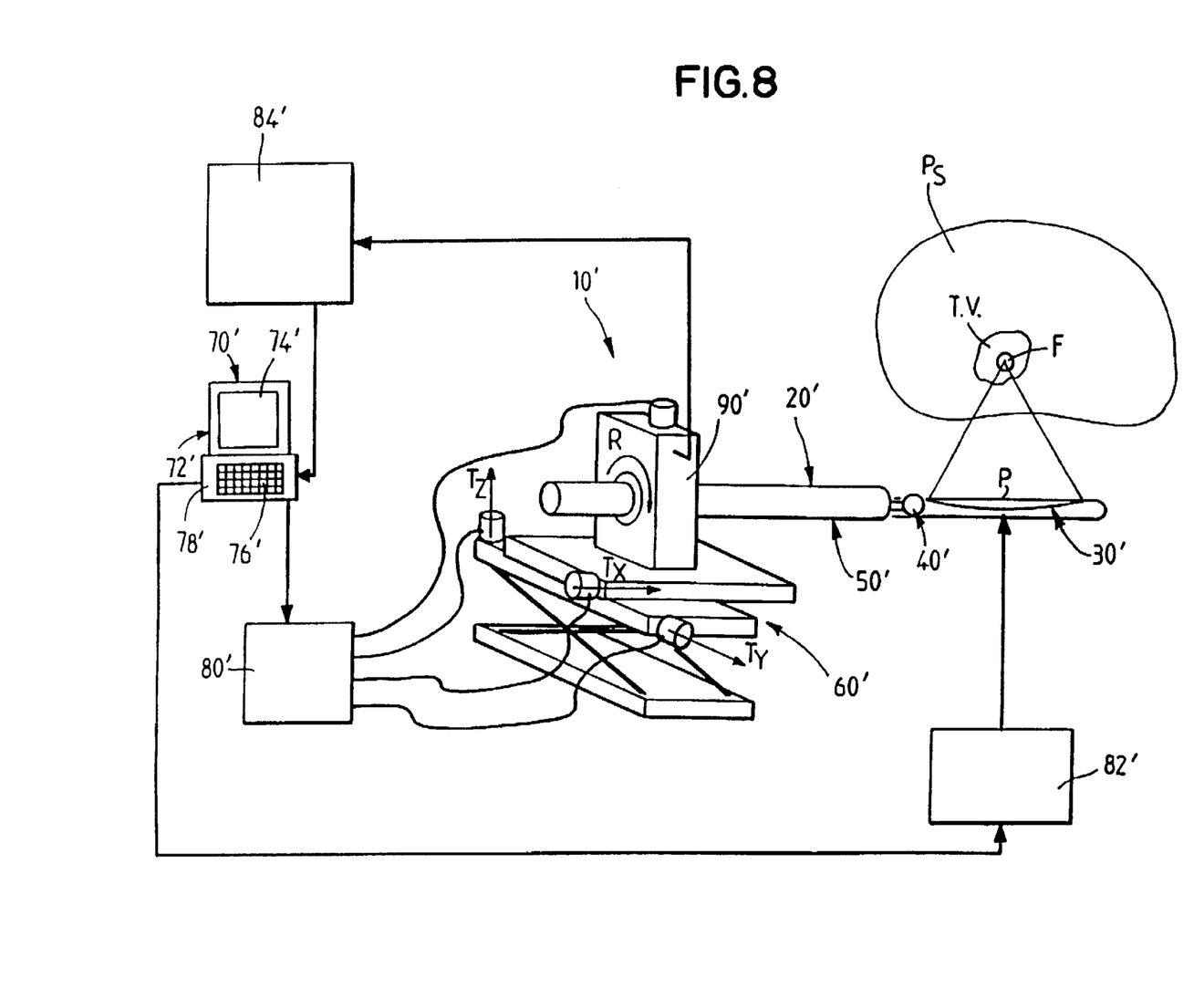
FIG. 8 is a diagrammatical view of a treatment apparatus according to the present invention comprising an endocavital probe according to this invention with essential control members.

In the framework of this invention, it is advantageous when endocavital probe 20' is able to be mounted rotatively about its longitudinal axis by rotational driving means 90' controlled by command means 80' as shown symbolically by arrow R. These rotational driving means 90' are advantageously mounted on a table able to move in the X, Y and Z directions, as shown symbolically by arrows TX, TY and TZ. Such tables are well known to those skilled in the art together with the corresponding command means 80', and are thus not described in more detail here.

Figure 9:
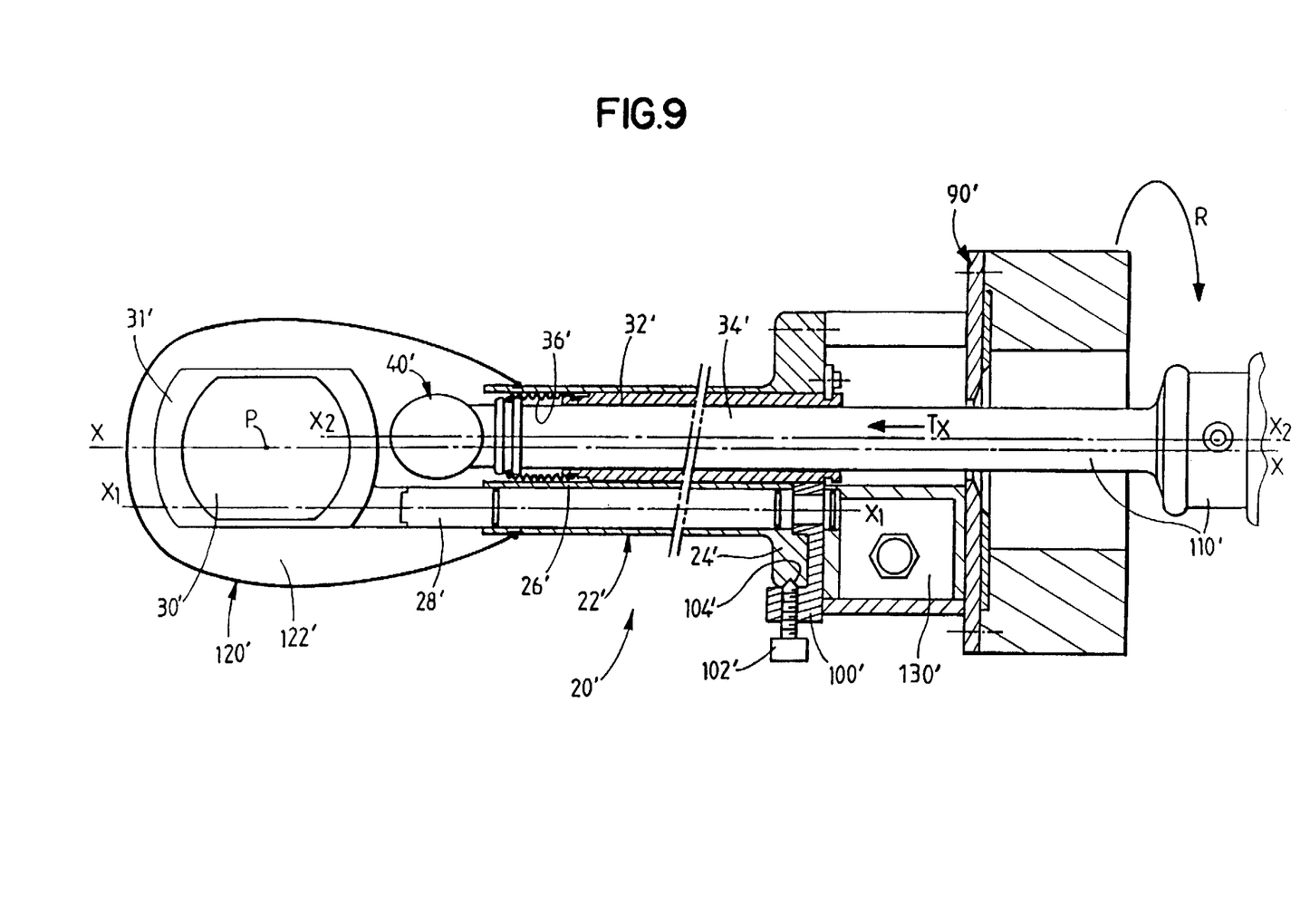
FIG. 9 is a longitudinal axial section of the endocavital probe according to one embodiment of the invention, showing the forward and rear parts of said endocavital probe in the introduction or treatment position.
Figure 10:
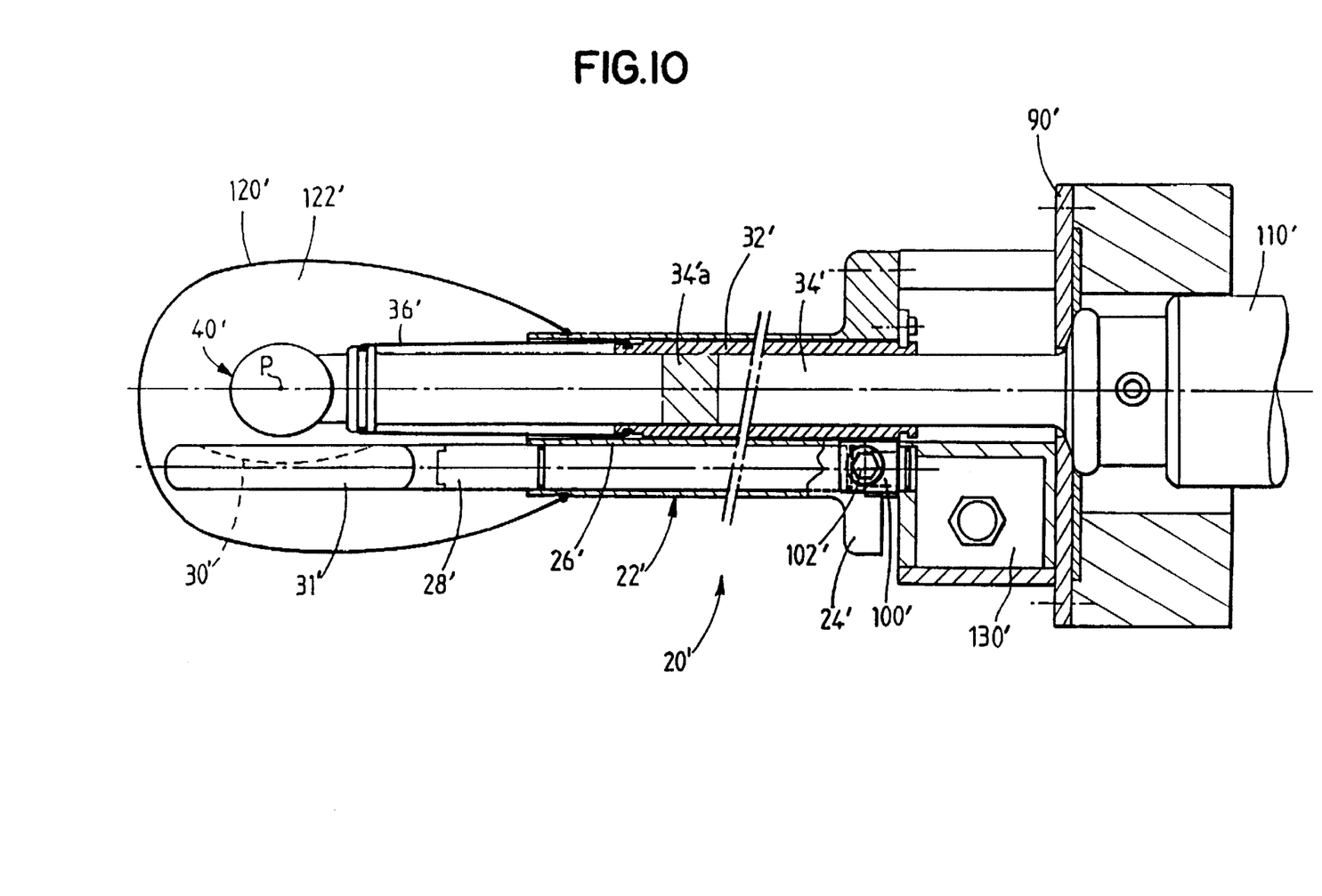
FIG. 10 is a sectional view similar to that of FIG. 9 but with certain surface parts removed in the area of the therapy transducer rotational control means, after a 90° rotation from the position in FIG. 9 of the therapy transducer and positioning of said imaging transducer in the extended position.

The endocavital probe is shown in more detail in a longitudinal section in FIGS. 9 and 10.

Endocavital probe 20' generally comprises a substantially tubular elongated body 22' carrying a flange 24' at its rear base for connection to motion imparting means 90' of FIG. 8 to enable probe 20' to be controllably driven in rotation about its longitudinal axis X—X.

Inside body 22' of endocavital probe 20, there is arranged a first tubular element 26' the axis of which, $X_1$—$X_1$ is offset with respect to longitudinal axis X—X of endocavital probe 20 and which houses a rod 28' constituting support or driving means for driving therapy transducer 30' in rotation, and guides the rotation of said rod 28'.

Body 22' comprises, secondly, a second tubular element 32' the axis of which, $X_2$—$X_2$ can be coaxial with, or slightly offset with respect to endocavital probe 20' axis X—X, are shown. Second tube 32' houses a rod 34' supporting or driving imaging transducer 40' and guides the longitudinal movements thereof.

Moreover, therapy transducer 30' is rotatively mounted about axis $X_1$—$X_1$ via its support rod 28' by individual motion-imparting means 100' which can be locked in position by locking means 102' such as a screw co-operating with a corresponding housing 104' in flange 24', at a first position, for treatment, which is also employed for introduction as shown in FIG. 9, and a second position in which it is retracted, as shown in FIG. 10', following rotation through an angle of rotation of 90° about axis $X_1$—$X_1$ to raise therapy transducer 30' to a position substantially perpendicular to the plane defined by the treatment position of FIG. 9. It will thus be noted that, here, the motion-imparting means 100' can be manually controlled. They can obviously also be automatically controlled by control unit 70' in another embodiment, using motor-driven motion-imparting means well known to those skilled in the art.

When the intention is only to ensure translational movement of imaging transducer 40' between the withdrawn position shown in FIG. 9 and the extended position shown in FIG. 10, provision can be made for second tubular element 32' to have a non-circular cross-section, for example a rectangular or square section, and, in this case, rod 34' supporting imaging transducer 40' will have a matching cross-section, for example a rectangular cross-section, such as shown diagrammatically at 34'a in FIG. 10. Advantageously, an element 36' forming a seal between rod 34' and second tubular element 32' against passage of a liquid 122' providing the acoustic coupling described above is present and advantageously takes the form of a bellows member able to adapt to the various positions of translational movement of the imaging transducer and also optionally being able to provide a spring effect to facilitate retraction of the imaging transducer into the retracted position of FIG. 9. A housing 130' can also be provided incorporating impedence matching components well known to those skilled in the art. This impedance matching device can also be integral with the endocavital probe.

It will also be noted that, according to the invention, imaging transducer 40' can be mounted inside an independent imaging probe 34', as shown, and which can consist of any type of commercially-available probe. Such commercially-available imaging probes are well known to those skilled in the art. As described above, a probe is preferred, according to the invention, which is capable of forming images in several planes, in particular in two perpendicular planes.

Figure 11:
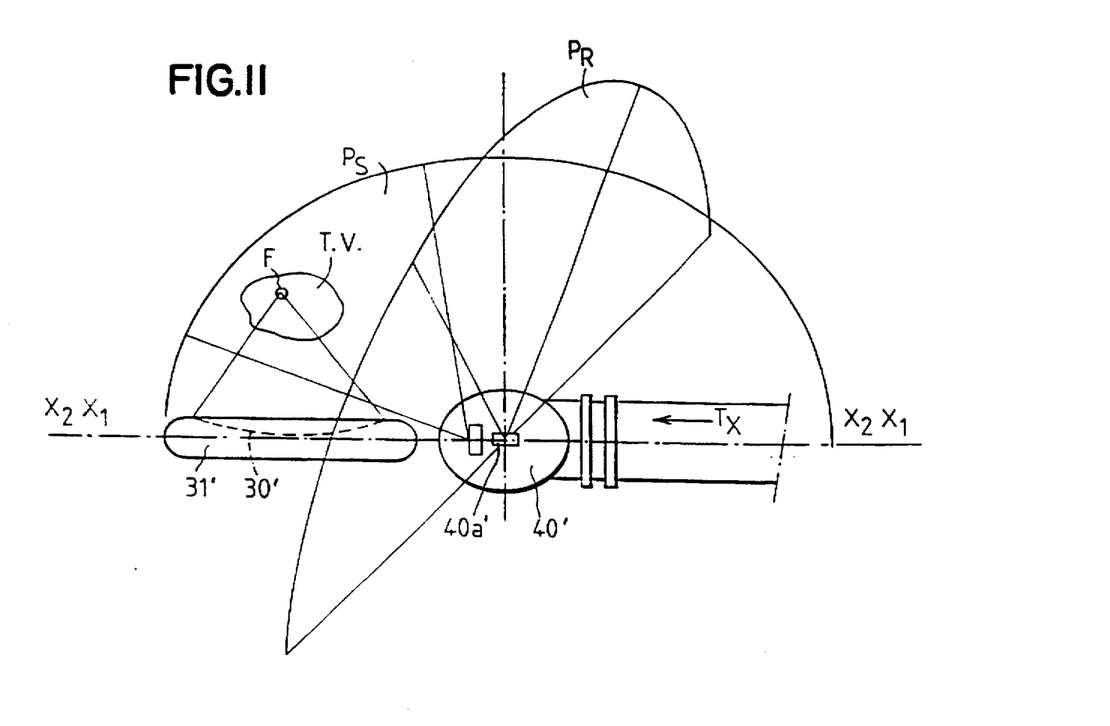
FIG. 11 shows diagrammatically the two types of sectional plane of the imaging transducer of the probe of FIGS. 8 to 10.

Thus, it can be seen in FIG. 9 that, when imaging transducer 40' is in its retracted position, it provides room for the therapy transducer which can be set to the treatment position shown in FIG. 9 after rotation through 90° from the target region imaging position shown in FIG. 10; real time imaging of the target region with imaging transducer 40' in its retracted position is still possible thanks to the latter's ability to provide images in two perpendicular planes, and in this case in plane PS of FIG. 11, as will be described later.

It will also be understood that therapy transducer 30', in its treatment position of FIG. 9, has a central point P which is close to the central positioning point of imaging probe 40' in its extended position of FIG. 10, which makes it possible to obtain an image of the target volume (T.V.) in a position close to the position of therapy transducer 30' at the instant therapy was performed.

Provisions can also be made for endocavital probe 20' to be terminated at its forward end by a flexible membrane 120' defining an inner volume in which therapy transducer 30' and imaging transducer 40' are respectively disposed in a displaceable manner, said cavity being filled with an acoustic coupling liquid 122' such as water, in particular degassed water, or an oil. The structure and assembly of said membrane 120' are similar to those described in this applicant's earlier document FR-A-2,67,542 equivalent to PCT/EP-9200410 which is incorporated herein by reference and to which the person skilled in the art may make reference.

Also, therapy transducer 30' is preferably constituted by the transducer described in the above earlier document FR-A-2,67,542 equivalent to PCT/EP9200410, with its corresponding support member 31' thus providing the advantages of volume minimization in a cross-sectional plane perpendicular to the axis of introduction. Thus, the therapy transducer is advantageously mounted in support member 31', integral with the support means which here take the form of rod 28' having a cross-section in a plane perpendicular to the axis of introduction X—X defining a perimeter which matches as closely as possible the perimeter of a cross-section in the same plane of therapy transducer 30', as was described in detail in the It is also advantageous when the outer shape of therapy transducer 30' is that of a disc with a profile which for the most part is substantially circular but with a reduced diameter in a direction perpendicular to the axis of introduction. Reference can be made to FIGS. 5 to 9 of the earlier document cited above which is incorporated in full herein by reference, for further clarification of this matter.

The imaging probe can be any imaging probe that is commercially available. However, in one advantageous embodiment, the imaging probe 40' is designed to supply so-called dual-plane images, as shown in FIG. 11, these being a first radial plane, PR, that is perpendicular to introduction axis X—X using a first transducer element 40'a, and a second sagittal plane, PS, containing the axis of introduction X—X or substantially parallel thereto, thus enabling, in particular, an image to be obtained of the treatment volume T.V. during treatment, as will be readily understood when FIGS. 8 and 11 are considered. As is also well known to those skilled in the art, imaging transducer element 40' is also mounted so as to be able to perform rotational movement about itself, to supply either imaging plane PR or imaging plane PS.

It will now be understood that the invention makes it possible to resolve the technical problem stated above and to achieve the determining technical advantages stated previously.

The operation of treatment apparatus according to the present invention implementing the method of treatment described above will now be explained in detail.

Figure 12:
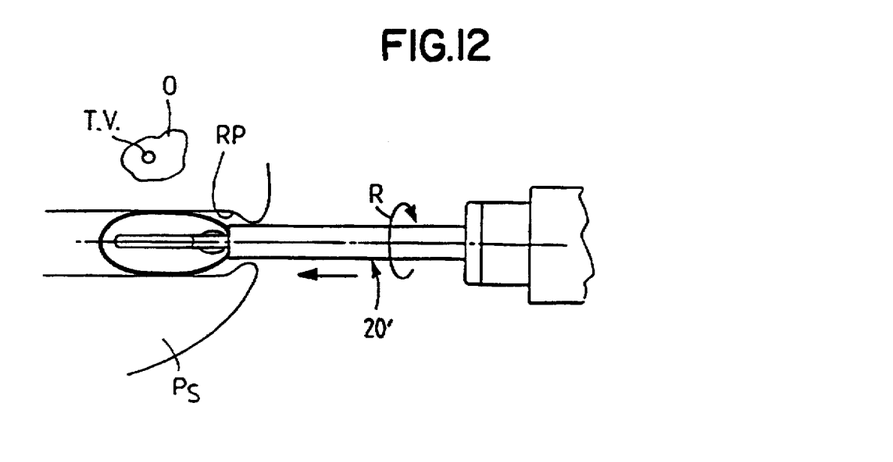
FIG. 12 shows, diagrammatically, the beginning of introduction of the endocavital probe according to FIGS. 8 to 11 into a body cavity, here the rectum, of a human being.

This treatment apparatus can be used for carrying out treatment of any target region, in particular a tissue region located inside the body of a living being, in particular a mammal, advantageously a human being. This target region can be a tissue region, in particular inside an organ, these tissues being non malignant or malignant, such as a nonmalignant or malignant tumor. The invention is particularly useful in the treatment of prostate tumors. In this framework, FIG. 12 shows diagrammatically the introduction phase of an endocavital probe 20' into the rectum Rp of a patient P by a translational movement in the direction of the arrow shown on FIG. 12. It is also possible to provide a rotational movement R of endocavital probe 20' to achieve accurate positioning with respect to an organ O such as the prostate, inside of which a tissue volume T.V. to be treated, such as a non-malignant or malignant tumor of this organ O, for example the prostate, is situated. In this introductory phase, therapy transducer 30' is positioned at the position shown in FIG. 9, the introduction position thus also corresponding to the treatment position.

When this accurate positioning has been achieved, therapy transducer 30' is set means 100' and then imaging probe 40' is advanced to the extended position shown of FIG. 10 in order to obtain one or several images of the treatment volume T.V., said image being displayed by display means 84' and/or 74'. The volume of target region T.V. can be determined automatically by control unit 70' using built-in computing means, and than said control unit 70' can provide automatic command, using data optionally introduced by the operator from keyboard 76' and instructions stored in a memory 78', the means 82' controlling therapy transducer 30' after repositioning the latter in the position shown in FIG. 9, after having withdrawn the imaging transducer 40' as shown in FIG. 9.

Actual treatment of the target area T.V. by the therapy transducer is well known to those skilled in the art and will not be described in detail here. For this, one could refer to the earlier document FR-A-2,67,542 corresponding to PCT/EP9200410. In particular, the therapy transducer element 30' can be positioned naturally or by electronic means and have a ratio between diameter and focal length comprised between 0.8 and 1.5.

Transducer element 30' can be advantageously arranged to deliver ultrasound waves generated at a frequency comprised between 1 and 4 MHz and with a short pulse duration comprised between 50 ms and 5 s, and preferably between 1 and 4 s, the power intensity at focal point F (FIG. 8) being comprised between 1000 and 10,000 W/cm$^2$.

This therapy transducer 30' can also be a composite piezoelectric transducer as described in the earlier document PCT/EP-9201534 equivalent to French application serial No. 910997 which is also incorporated herein by reference in its entirety.

In order to achieve complete treatment of the target region T.V., for example a tumor situated inside the organ O, it may be necessary to displace the endocavital probe 20' using a rotational movement about its axis of rotation R and/or a translational movement which, here, is along translation axis TX as can be clearly seen and understood upon consideration of the figures.

Figure 13:
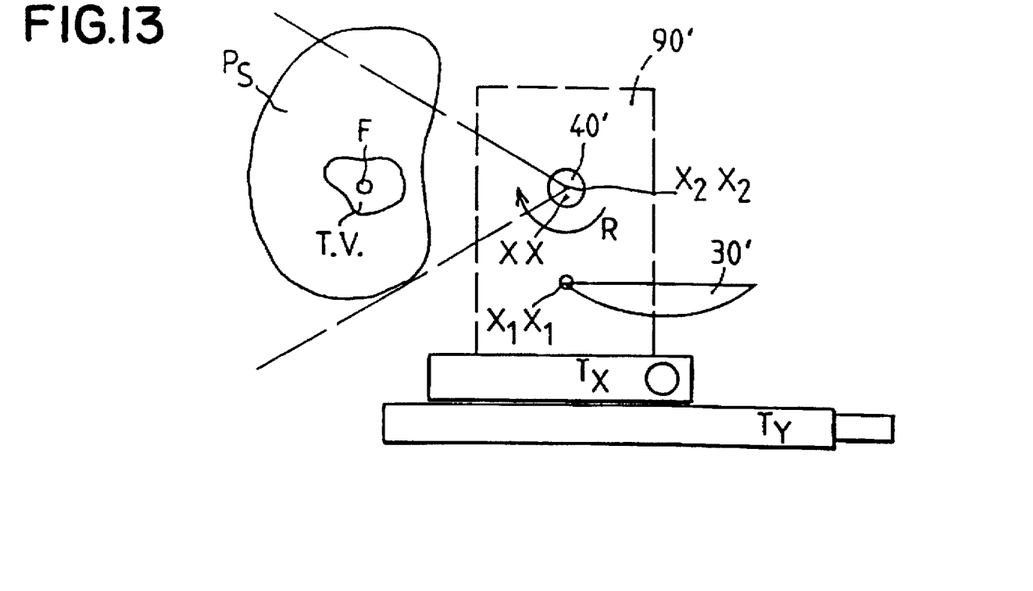
FIG. 13 is a diagrammatical view in cross-section showing the imaging position of the imaging transducer relative to the prostate of a patient for treatment, said patient being on his side, after 90° rotation with respect to the position in FIG. 8 in which the patient is on his back.

Additionally, FIGS. 8 to 12 are an integral part of this present invention, and thus of this description. Referring now to FIG. 13, the imaging position of imaging probe 40' in its extended position is illustrated, therapy transducer 30' being at its retracted position after having performed a 90° rotation compared to the introduction position shown in FIG. 9, this retracted position also been shown in FIG. 10 for imaging prior to treatment. In the position shown on FIG. 13, the patient is laying on his side after having been initially on his back as shown in FIG. 8 at the time of introduction of the endocavital probe, here into the rectum.

Figure 14:
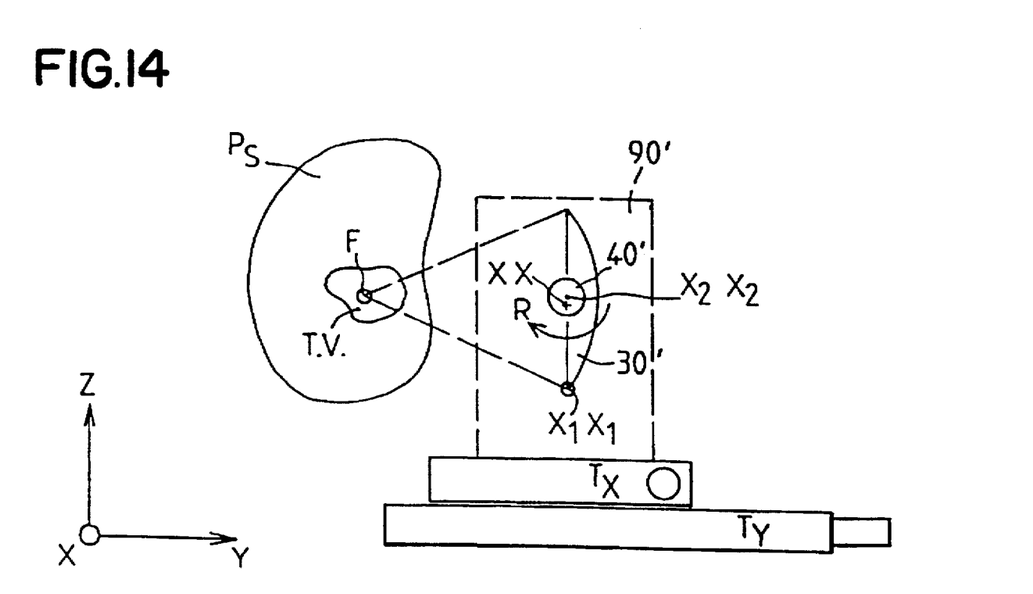
FIG. 14 is a view similar to that in FIG. 13 but in the treatment position, the focal point of the treatment probe being disposed inside the treatment volume T.V.

With reference to FIG. 14, the treatment position is shown, this having being withdrawn position shown on FIG. 9, therapy transducer 30' having been rotated through 90° about rotation axis X1—X1 to arrive at the position shown of FIG. 9. To carry out treatment of the volume of the tumor T.V., it will be understood that the focal spot or area F of focusing therapy transducer 30' is too small to allow treatment to be achieved in one single step. It is thus necessary to move the focal spot to various points in order to obtain full treatment of the minor volume. This shift is obtained by bringing about rotation of the endocavital probe, by rotating the rear portion 90' of endocavital probe 20' in the direction of arrow R thus causing the focal spot F to move along the Z axis, while translational movement along the axis TX and the axis TY moves the spot in the X and Y axes, thus making it possible to treat the volume T.V. in the X, Y, Z space. During such treatment, it can be observed that the imaging transducer 40', thanks to being able to obtain the imaging plane PS, ensures the treatment volume T.V. as well as the focal spot can be visualized, thus allowing treatment to be followed in real time, which is a determining factor in ensuring absolute safety of treatment.

The embodiments shown in FIGS. 1 to 7 on the one hand, and those shown on the other hand in FIGS. 8 to 14 can advantageously be combined. One can thus use a therapy transducer in the general shape of a spoon, such as the one illustrated in FIG. 9 or FIG. 10, in the probe of FIG. 1 or 2. The transmission characteristics of the therapy transducer described for FIG. 14 can apply to the treatment transducer of the invention in all embodiments thereof. One can thus employ a composite therapy transducer, having a focal length that is variable electronically.

Obviously, the means supporting the probe, or the probe body which differ in the various embodiments of the invention, can be interchanged.

Additionally, the invention covers every characteristic which appears to be novel over any state of the art whatsoever, in this specification considered in its entirety and including FIGS. 1 to 14 which constitute an integral part thereof.

We claim:

1. A therapy and imaging probe comprising:
    a probe body of an elongate shape defining a general axis;
    at least one imaging transducer for transmitting imaging waves, said imaging transducer being mounted on first support means providing translational movement of said imaging transducer within said probe body, substantially parallel to said general axis of said probe body, between a withdrawn position and an extended position;
    at least one therapy transducer for transmitting therapy waves, said therapy transducer being mounted on second support means providing rotation of said therapy transducer within and relative to said probe body, about an axis of rotation substantially parallel to said general axis of said probe but offset with respect to said imaging transducer;
    said second support means providing rotation of said therapy transducer between a treatment position for which said imaging transducer is at a withdrawn position, and a withdrawn position for which said imaging transducer may be brought by translational movement to its extended position to occupy the place occupied by said therapy transducer in its treatment position; and
    a direction of transmission of therapy waves by said therapy transducer in its treatment position being substantially identical to a direction of transmission of imaging waves by said imaging transducer in its extended position.

2. A therapy and imaging probe according to claim 1, wherein said axis of rotation of said therapy transducer is outside a largest dimension of said imaging transducer.

3. A therapy and imaging probe according to claim 1, wherein said therapy transducer and said imaging transducer are arranged inside a flexible membrane filled with an acoustic-coupling liquid such as water or an oil.

4. A therapy and imaging probe according to claim 1, wherein said therapy transducer is mounted in a support member integral with said second support means and having a cross-section in a plane perpendicular to said general axis of said probe defining a perimeter which is close to a perimeter of a cross-section taken in said plane of said therapy transducer.

5. A therapy and imaging probe according to claim 4, wherein an external shape of said therapy transducer is that of a disc, a profile of which is for a major part substantially circular, but having a reduced diameter in a direction perpendicular to said general axis of said probe.

6. A therapy and imaging probe according to claim 1, wherein said imaging transducer is arranged to provide images in several planes.

7. A therapy and imaging probe according to claim 6, wherein said imaging transducer is arranged to provide images in two perpendicular planes, comprising a radial plane, perpendicular to said general axis of said probe, and a sagittal plane, containing said general axis thereby making it possible to also provide imaging when said imaging transducer is in said withdrawn position and said therapy transducer is in said treatment position.

8. A therapy and imaging probe according to claim 1, wherein said therapy transducer provides focusing in a direction substantially perpendicular to said general axis.

9. A therapy and imaging probe according to claim 4, wherein said support member for said therapy transducer has a substantially circular outside shape, close to an outer shape of a substantially circular-shaped therapy transducer, said support member being integral with said second support means close to an edge of said support member, thereby facilitating movement of said therapy transducer between said withdrawn position and said treatment position.

10. A therapy and imaging probe according to claim 9, wherein in said treatment position, the outer shape of said therapy transducer defines a plane that contains said general axis.

11. A therapy and imaging probe according to claim 4, wherein said support member for said therapy transducer has a substantially polygonal outside shape, close to an outer shape of a substantially polygonal-shaped therapy transducer, said support member being integral with said second support means close to an edge of said support member, thereby facilitating movement of said therapy transducer between said withdrawn position and said treatment position.

12. A therapy and imaging probe according to claim 11, wherein in said treatment position, the outer shape of said therapy transducer defines a plane that contains said general axis.

13. A therapy and imaging probe according to claim 1, comprising means for providing manual rotation of said therapy transducer, and means for providing manual translational movement of said imaging transducer.

14. A therapy and imaging probe according to claim 1, comprising means for providing motor-driven rotation of said therapy transducer, and means for providing motor-driven translational movement of said imaging transducer.

15. A therapy and imaging probe according to claim 1, wherein said therapy transducer has a ratio between diameter and focal length comprised between 0.8 and 1.5.

16. A therapy and imaging probe according to claim 15, wherein said therapy transducer has a ratio between diameter and focal length of substantially.

17. A therapy and imaging probe according to claim 1, comprising means for making said therapy transducer deliver ultrasound waves pulsed at a frequency comprised between 1 and 4 MHz and with a short pulse duration comprised between 50 ms and 5 s, with an intensity at a focal point F comprised between 1,000 and 10,000 W/cm2.

18. A therapy and imaging probe according to claim 17, wherein said short pulse duration is comprised between 1 and 4 s.

19. A therapy and imaging probe according to claim 1, wherein said therapy transducer comprises a mechanically-deformable lens allowing modification of the focal length thereof.

20. A therapy and imaging probe according to claim 1, comprising a rigid wall at least partially surrounding said transducers.

21. A therapy and imaging probe according to claim 20, wherein said rigid wall includes a window.

22. A therapy and imaging probe according to claim 1, comprising a locally-deformable flexible casing.

23. Treatment apparatus, comprising a therapy and imaging probe as defined in claim 1.

24. Treatment apparatus according to claim 23, for treating a target region inside the body of a mammal, comprising means for introducing said probe into a body cavity.

25. Treatment apparatus according to claim 24, wherein said target region is a tissue region of a non-malignant tumor of a body of a human being.

26. Treatment apparatus according to claim 24, wherein said target region is a tissue region of a malignant tumor of a body of a human being.

27. Treatment apparatus according to claim 24, for treating prostate tissue of a body of a human being by urethral or rectal route.

28. A method for treating a target region inside the body of a mammal, comprising:
   providing a probe including;
      (i) a probe body of an elongate shape defining a general axis;
      (ii) an imaging transducer for transmitting imaging waves, said imaging transducer being mounted on first support means providing translational movement of said imaging transducer within said probe body, substantially parallel to said general axis of said probe body, between a withdrawal position and an extended position; and
      (iii) a therapy transducer for transmitting therapy waves, said therapy transducer being mounted on second support means providing rotation of said therapy transducer within and relative to said probe body, about an axis of rotation substantially parallel to said general axis of said probe body but offset with respect to said imaging transducer, said second support means providing rotation of said therapy transducer between a treatment position for which said imaging transducer is at a withdrawn position, and a withdrawn position for which said imaging transducer may be brought by translational movement to its extended position to occupy the place occupied by said therapy transducer in its treatment position;
   introducing said probe into a body cavity until said therapy transducer in its treatment position is substantially facing said target region;
   rotating said therapy transducer relative to said probe body in order to position it in said withdrawn position;
   moving said imaging transducer with a translational movement into said extended position to occupy the place occupied by said therapy transducer in its treatment position;
   forming an image with said imaging transducer of said target region to be treated by said therapy transducer allowing said target region to be viewed;
   withdrawing said imaging transducer into said withdrawn position;
   rotating said therapy transducer relative to said probe body to bring it to said treatment position; and
   delivering ultrasonic treatment waves during a predetermined interval necessary for performing said treatment.

29. A method according to claim 28, wherein said mammal is a human being, said a target region comprises prostate tissue, and said body cavity is a urethra of said human being.

30. A method according to claim 28, wherein said mammal is a human being, said a target region comprises prostate tissue, and said body cavity is a rectum of said human being.

* * * * *